(12) United States Patent
Rousseau et al.

(10) Patent No.: US 8,100,843 B2
(45) Date of Patent: Jan. 24, 2012

(54) SHAPE MEMORY POLYMER MEDICAL CAST

(75) Inventors: Ingrid A. Rousseau, Clinton Township, MI (US); Elisabeth J. Berger, Farmington Hills, MI (US); John N. Owens, Franklin, MI (US); Hamid G. Kia, Bloomfield Hills, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 296 days.

(21) Appl. No.: 12/410,415

(22) Filed: Mar. 24, 2009

(65) Prior Publication Data

US 2010/0249682 A1 Sep. 30, 2010

(51) Int. Cl.
*A61F 5/00* (2006.01)
(52) U.S. Cl. .......................................... 602/7
(58) Field of Classification Search .................. 602/7, 5, 602/1, 20, 6, 18, 14, 8
See application file for complete search history.

(56) References Cited

U.S. PATENT DOCUMENTS 3,329,143 A * 7/1967 Gordon ............................. 602/3
5,415,623 A * 5/1995 Cherubini .......................... 602/7
5,807,291 A * 9/1998 Larson et al. ..................... 602/8

OTHER PUBLICATIONS http://www.allfit.com.cn/fla/book01y.swf, printed Feb. 25, 2009, 8 pages.

* cited by examiner

*Primary Examiner* — Patricia Bianco
*Assistant Examiner* — Tarla Patel
(74) *Attorney, Agent, or Firm* — Dierker & Associates, P.C.

(57) ABSTRACT

A medical cast and methods of using the same are disclosed. The method of making includes providing a shape memory polymer (SMP) in a permanent shape which corresponds to a limb's general shape but has a diameter smaller than the limb's diameter. The SMP is converted from the permanent shape into a primary temporary shape, which has a diameter larger than both a diameter of the permanent shape and a diameter of the limb. The limb is at least partially surrounded with the SMP in its primary temporary shape. The SMP is then heated, which causes the primary temporary shape to i) attempt to revert to the permanent shape, and ii) conform to a secondary temporary shape having a diameter smaller than that of the primary temporary shape and larger than that of the permanent shape. The SMP in the secondary temporary shape conforms to the limb.

16 Claims, 2 Drawing Sheets

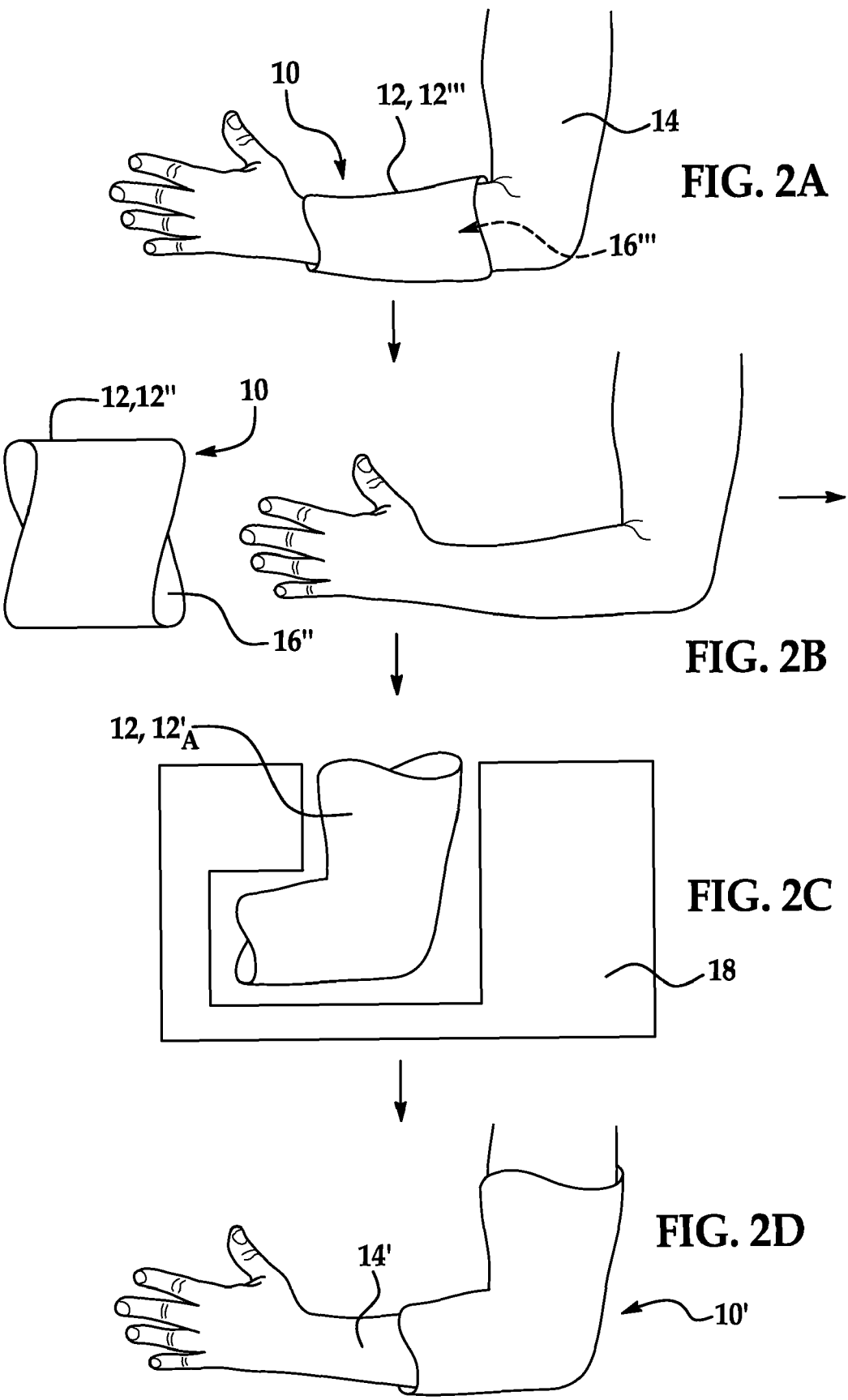

SHAPE MEMORY POLYMER MEDICAL CAST

TECHNICAL FIELD

The present disclosure relates generally to medical casts, and more particularly to methods of making and using a shape memory polymer medical cast.

BACKGROUND

Medical casts are commonly used to heal broken bones, tendon tears, or other injuries of a subject's limbs. Many conventional medical casts include a bandage that is to be wrapped around the injured limb, which is secured to the limb via a dried resin, plaster, or other similar material established on the bandage. The bandage enables the plaster-like material to conform to the then-current shape of the injured limb. The medical cast is typically worn by the subject for an amount of time sufficient to heal the injury. In some instances, the cast is removed after the healing process is complete. In other instances, the cast may be removed and replaced one or more times before the healing process is complete in order to adjust the size and/or shape of the cast to changes in size and/or shape of the healing limb.

SUMMARY

A medical cast and methods of making and using the same are disclosed herein. A method of making a medical cast for a limb of a subject is disclosed herein. The method includes providing a shape memory polymer in a permanent shape, where the permanent shape corresponds to a general shape of the limb but having a diameter smaller than a diameter of the limb. The shape memory polymer is converted from the permanent shape into a primary temporary shape, where the primary temporary shape has a diameter that is larger than both a diameter of the permanent shape and a diameter of the limb. The method further includes at least partially surrounding the limb with the shape memory polymer in the primary temporary shape. The shape memory polymer is then heated, thereby causing the primary temporary shape to i) attempt to revert to the permanent shape, and ii) conform to a secondary temporary shape having a diameter smaller than the diameter of the primary temporary shape and larger than that of the permanent shape, wherein the shape memory polymer in the secondary temporary shape conforms to the limb.

BRIEF DESCRIPTION OF THE DRAWINGS

Features and advantages of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 2A through 2D together schematically depict an example of a method of reusing a medical cast.

DETAILED DESCRIPTION

Figure 1A:
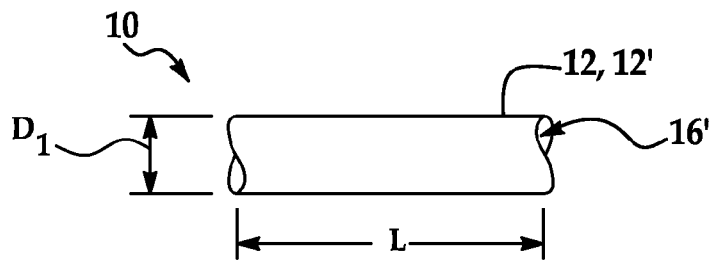
FIGS. 1A through 1D together schematically depict an example of a method of using a medical cast on a limb of a subject.

Embodiment(s) of the method, as disclosed herein, may be used to make and use a medical cast formed from a shape memory polymer. The shape memory polymer medical cast may advantageously be i) conformed to a then-current shape of an injured limb without having to use bandages, ii) reformed to the shape of the injured limb at various stages throughout the healing process, and in some instances, iii) reused for another injured limb of a different shape. The shape memory polymer therefore enables custom-fitting of the medical cast to any injured limb for any subject. Furthermore, the custom-fit and ability to refit enable the medical cast to advantageously be used at any stage of the healing process, simply by heating (generally for a short time) the shape memory polymer (to a temperature above its switching temperature) to conform or re-conform its shape to accommodate changes in the shape and/or size of the healing limb. Such custom-fitting also enables the medical cast to exert a relatively constant pressure on the injured limb for proper healing.

Referring now to the drawings, FIGS. 1A through 1D together schematically depict an example of a method of using a medical cast 10 (shown in FIG. 1D) for a limb 14 (shown in FIGS. 1C and 1D) of a subject. FIGS. 2A through 2D together depict an example of a method of reusing the medical cast 10 to form a new cast 10' (shown in FIG. 2D) for another limb 14' (also shown in FIG. 2D).

Figure 1B:
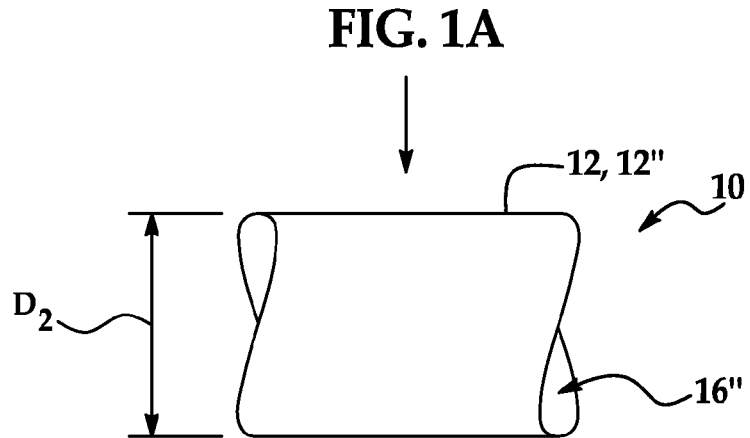
Figure 1C:
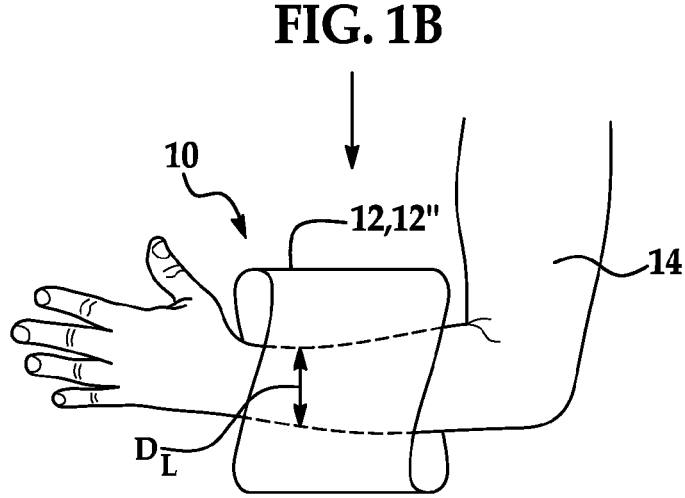
Figure 1D:
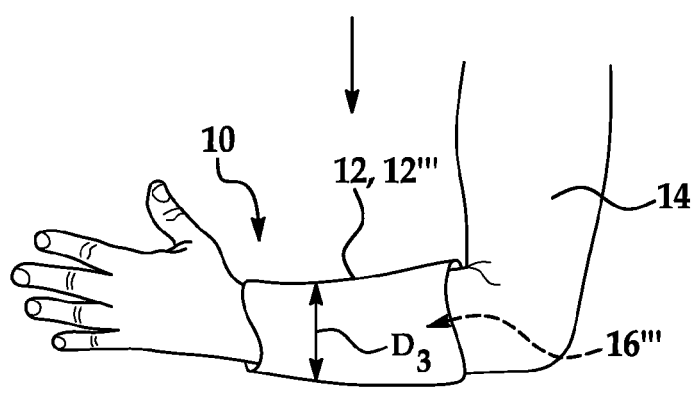

The medical cast 10, 10' is generally formed from a shape memory polymer 12. It is to be understood that the shape memory polymer 12 may adopt several shapes, including: a permanent shape (referred to herein as 12', as shown in FIG. 1A); a primary temporary shape (referred to herein as 12", as shown in FIGS. 1B, 1C, and 2B); and a secondary temporary shape (referred to herein as 12''', as shown in FIGS. 1D and 2A). The permanent shape 12' of the shape memory polymer 12 may also be reset into another new permanent shape (referred to herein as $12'_A$, as shown in FIG. 2C). The permanent shape 12', the new permanent shape $12'_A$, the primary temporary shape 12", and the secondary temporary shape 12''' of the shape memory polymer 12 will be described further hereinbelow.

As used herein, the term "subject" refers to any living creature having one or more limbs. Non-limiting examples of living creatures include human beings, other two-legged creatures (e.g., birds, monkeys, etc.), four-legged creatures (e.g., dogs, cats, etc.), creatures having more than four legs, or other creatures having legs, arms, or a combination of both. Furthermore, the term "limb" as used herein may include one of the jointed appendages of the subject (e.g., arm, leg, wing, etc.), a trunk area of the body (e.g., the torso, abdomen, etc.), the neck, and/or any other body part of the subject (e.g., elbow, nose, tail, etc.) for which a cast may be needed.

Referring now to FIG. 1A, the method of using the medical cast 10 includes providing the shape memory polymer 12 in its permanent shape 12'. The shape memory polymer 12 may be originally formed into the permanent shape, for example, by molding the shape memory polymer 12 using a molding tool (an example of which is schematically depicted and identified by reference numeral 18 in FIG. 2C). The molding tool may, for example, have an inner shape that grossly corresponds to the overall outer shape of the injured limb 14. For example, if the limb is a forearm or a leg, the inner shape will be cylindrical. The molding tool may also include a portion which defines a hollow portion of the permanent shape 12'. Generally, the shape memory polymer 12 is molded into the permanent shape 12' such that a hollow portion 16' is defined. The polymer 12 in its permanent shape 12' may be cured at or above its curing temperature (which, depending on the material used, may or may not be above the highest melting temperature, glass transition temperature, or switching temperature).

In some instances after the initial molding of the shape memory polymer 12 takes place, the shape memory polymer 12 (positioned in the molding tool) is heated to a temperature sufficient to deform the shape memory polymer 12 such that it may be readily removed from the molding tool. In an example, heat may be applied to deform the shape memory polymer 12 to facilitate removal thereof from a portion of the molding tool configured to establish the hollow portion 16' of the shape memory polymer 12. Heat (above the switching temperature) softens the polymer 12, and pressure and/or a suitable mechanical force may be applied to achieve a shape that is removable from the portion of the molding tool establishing the hollow portion 16' of the shape memory polymer 12. This form of removal may be used to facilitate removal of the shape memory polymer 12 from the molding tool and/or when the shape memory polymer 12 includes a die-locked feature. In other instances however, the polymer 12 in its permanent shape 12' may simply be removed from the molding tool (i.e., without heat). This form of removal is generally used when a die-locked molding tool is not utilized for setting the permanent shape 12'.

Any desirable shape memory polymer 12 may be utilized. In one embodiment, the shape memory polymer 12 includes one or more thermoset polymers. However, in some other instances, the shape memory polymer 12 includes one or more thermoplastic polymers. In yet other instances, the shape memory polymer 12 may include a thermoset polymer combined with a thermoplastic polymer. In instances where the shape memory polymer 12 is a thermoplastic polymer, the recovery of the permanent shape 12' is enabled by physical cross-links present in the polymeric structure. In instances where the shape memory polymer 12 is, or includes, a thermoset polymer, the recovery of the permanent shape 12' is enabled by covalent cross-links in the polymeric structure. In either case, it is to be understood that, when the shape memory polymer 12 is heated to a temperature above its switching temperature, the presence of the physical or covalent cross-links allows for the reversion of the shape memory polymer 12 from one shape (e.g., the primary temporary shape 12") to another shape (e.g., the permanent shape 12' or the secondary temporary shape 12''') by releasing energy i) previously imparted to the system by the deformation of the polymer 12, and ii) stored in the system by subsequent cooling processes. It is to be understood that the deformation of the shape memory polymer 12, when the shape memory polymer 12 is in its low modulus state (i.e., the shape memory polymer 12 is heated above its switching temperature), causes at least some changes to the conformation of the polymeric structure (away from its equilibrium conformation) as a result of energy introduced to the shape memory polymer 12 from the mechanical force(s) imparted thereto during deformation. The changes in the conformation of the shape memory polymer 12 are set during the subsequently applied cooling processes. The setting is due, at least in part, to reduced chain mobility of the individual polymer chains in the structure of the shape memory polymer 12. Accordingly, the mechanical energy introduced into the system is substantially simultaneously stored during the subsequent cooling processes. Such energy is typically released during subsequent re-heating of the shape memory polymer 12 to a temperature above its switching temperature, which increases the chain mobility and allows the polymers chains to release the stored energy and, in doing so, to regain their original (equilibrium) conformation after the shape memory polymer 12 is cooled to a temperature below its switching temperature. The shape memory polymer 12 may be subsequently cooled to a temperature below its switching temperature to set the new shape.

In an example, the shape memory polymer 12, when formed as the cast 10, may be configured to enable breathing and/or aeration of the skin of the injured limb 14. Such breathability and/or aeratability may advantageously prevent bacterial growth caused from, e.g., sweating or any other moisture buildup between the cast 10 and the injured limb 14, and/or may provide more comfort to the subject of the injured limb 14. To accomplish such breathability and/or aeratability, the shape memory polymer 12 may, in some instances, be perforated (i.e., where the shape memory polymer 12 includes one or more visible perforations therein). In other instances, to accomplish the breathability and/or aeratability, the shape memory polymer 12 may be porous (i.e., where the shape memory polymer 12 includes a plurality of pores, generally not visible to the human eye). In still other instances, the breathability and/or aeratability may be accomplished by providing the shape memory polymer 12 in the form of a foam having a porous structure, where at least some of the pores are visible to the human eye. In some instances, the shape memory polymer 12 may be combinations of perforated, porous, and/or made from a foam.

The permanent shape 12' of the shape memory polymer 12 generally corresponds to a shape of the limb 14, but not necessarily to the size of the limb 14. The phrase "generally corresponds to the shape" or "has the general shape of" means that the permanent shape 12' grossly resembles the shape of the limb 14 of interest (i.e., has a similar shape to the shape of the limb 14). In many instances, the permanent shape 12' is cylindrical. In one embodiment, the permanent shape 12' is the general shape of the limb 14, but is smaller than the size of the actual limb 14. For example, the permanent shape 12' of the shape memory polymer 12 has a diameter $D_1$ that is smaller than a diameter $D_L$ of the limb 14 at its smallest cross-section. It is to be understood that the diameter $D_1$ of the shape memory polymer 12, 12' may be uniform, vary at opposed ends, or vary at multiple points along its length L. The consistency of the diameter $D_1$ will depend, at least in part, on the diameter $D_L$ of the targeted type of limb 14.

It is to be understood that the force/pressure that will be applied to the limb 14 when the cast 10 is secured thereon will be, in part, a function of the difference between $D_1$, $D_L$, and $D_2$. Therefore, for limbs 14 with a large difference in diameters from one side to the other (e.g., the change in diameter from an ankle to a knee or thigh), $D_1$ should be varied accordingly throughout the length of the polymer 12. However for limbs 14 with a relatively constant cross section (e.g., a forearm), $D_1$ may be selected to be relatively consistent throughout the length of the polymer 12.

The permanent shape of the shape memory polymer 12, 12' generally includes a hollow interior portion 16' defined by the interior walls of the shape memory polymer 12. In some instances, the permanent shape 12' is cylindrically-shaped. The shape of the shape memory polymer in its permanent shape 12, 12' may, in other instances, be substantially cylindrically-shape (i.e., have one or more minor variations in its shape that would depart from being an exact cylinder). It is yet further to be understood that the shape of the shape memory polymer 12 may conform to an incomplete cylinder (i.e., not having a complete circumference, e.g., a half-round cast secured via an elastic band). When an incomplete cylinder is formed, it is to be understood that this shape is set for the permanent shape 12' (as opposed to starting out as a substantially flat sheet that is manually conformed to the limb 14). Other desirable shapes for the permanent shape 12' of the shape memory polymer 12 are contemplated as being within the scope of the present disclosure, and such shapes may depend, at least in part, upon the limb 14 for which the shape memory polymer 12 is to be used as a cast.

Additionally, it is to be understood that the permanent shape 12' is the memorized shape of the shape memory polymer 12. In other words, after deformation of the shape memory polymer 12 into a temporary shape (such as, for example, the primary temporary shape 12"), the shape memory polymer 12 may be automatically reverted back into its memorized shape in the presence of heat (at or above the polymer's switching temperature). As will be described in further detail hereinbelow, because the diameter $D_L$ of the limb 14 is larger than the diameter $D_1$ of the shape memory polymer 12 in its permanent shape 12', when attempting to revert the shape memory polymer 12 back to its memorized or permanent shape 12', the shape memory polymer 12 will revert toward the permanent shape 12' until it snuggly fits around the limb 14. The polymer 12 does not actually achieve the permanent shape 12' upon reversion, rather, it takes on the secondary temporary shape 12''', which corresponds to a shape that is as close to the permanent shape 12' as the polymer 12 can revert to due to the presence of the limb 14. The snug fit of the shape memory polymer 12 in the secondary temporary shape 12''' enables the cast 10 to exert a relatively continuous amount of pressure on the injured limb 14 during healing. The amplitude of the force applied to the limb 14 depends, at least in part, on the stiffness of the shape memory polymer 12, which, in turn depends on its modulus and thickness, the temperature applied for its reversion, and the relative difference between the sizes of the shape memory polymer 12 in its permanent shape 12' and temporary shapes 12" and 12''', and of the limb 14. Therefore, a desired pressure could be targeted if necessary or desirable.

Referring now to FIG. 1B, the shape memory polymer 12 is converted from its permanent shape 12' to a desired primary temporary shape 12". The primary temporary shape 12" refers to any shape of the shape memory polymer 12 having a diameter $D_2$ that is larger than both the diameter $D_1$ of the permanent shape 12' and the diameter $D_L$ of the limb 14. In some instances, a specific diameter $D_2$ of the primary temporary shape 12" may be selected in order to generate the desirable amount of pressure or force to be applied to the injured limb 14. In an example, the primary temporary shape 12" of the shape memory polymer 12 is also cylindrically-shaped and includes a hollow interior portion 16" defined by the interior walls of the enlarged shape memory polymer 12, 12". Like the permanent shape 12', it is to be understood that other shapes are suitable for the primary temporary shape 12". Generally, the two shapes 12', 12" will be the same, except that the sizes (e.g., diameters) will be different.

In an example, the converting of the shape memory polymer 12 into its primary temporary shape 12" may be accomplished by heating the shape memory polymer 12 to a temperature above its switching temperature. Heating may be accomplished by applying one or more different techniques. In one example, the shape memory polymer 12 is heated by directly applying heat from at least one of i) water or other fluid (e.g., air) heated to the temperature above the switching temperature of the shape memory polymer 12, or ii) a heating device, such as a heated blanket or pad. In another example, heating may be accomplished by indirect heating when heat is emitted from active materials present in the shape memory polymer 12. Such active materials generate heat upon exposure to an external stimulus other than heat, such as, e.g., a magnetic field or irradiation. The amount of active materials that may be included in the polymer 12 depends, at least in part, on the desirable speed of heating, the configuration of polymer 12 itself, the filler type used (e.g., size, aspect ratio, thermal conductivity, etc.), and the desired shape memory performance of the shape memory polymer 12 in terms of its fixity and shape recovery capabilities. In yet another example, the shape memory polymer 12 (when fillers are not used) may be heated via exposure to irradiation (e.g., infra-red radiation).

As used herein, the "switching temperature" of the shape memory polymer 12 refers to the temperature at which the shape memory polymer becomes substantially easily deformable. This deformable state enables the shape memory polymer 12 to be switched from its permanent shape 12' into its primary temporary shape 12". The switching temperature also refers to the temperature at which the shape memory polymer 12 reaches its low modulus state and may spontaneously revert from its temporary shape 12" back into i) its permanent shape 12', or ii) a shape 12''' between the primary temporary shape 12" and the permanent shape 12'. As mentioned hereinabove, the shape 12''' generally results when, during reversion of the shape memory polymer 12 to its permanent shape 12', the shape memory polymer 12 encounters a reversion constraint (such as, e.g., the limb 14). It is to be understood that the switching temperature varies depending on the chemistry of the shape memory polymer 12 selected. In some instances, the chemistry of the shape memory polymer 12 may be such that its switching temperature coincides with the glass transition temperature of the shape memory polymer 12, a melting transition temperature of the shape memory polymer 12. It is also desirable that the switching temperature not cause discomfort to the patient.

One non-limiting example of a suitable shape memory polymer 12 includes an epoxy-based system. Such epoxy-based systems may be used alone, thereby imparting an optically transparent property to the shape memory polymer 12. In other instances, the epoxy-based system may include fillers, such as particulate filler and/or fibers, added thereto. Non-limiting examples of fillers include inorganic fillers or active materials, such as, e.g., shape memory alloy wires, magneto-responsive fillers, electroactive fillers, glass fibers, and/or the like, and/or combinations thereof. Such fillers may, in some cases, render the shape memory polymer 12 non-transparent. This will depend, at least in part, on the fillers used, the amount used, the filler distribution, and/or the size and/or shape of the fillers. Yet further, in some embodiments, organic fillers or additives may be added. For example, a colorant (e.g., a pigment or a dye), may be added to the shape memory polymer 12 to add color thereto, antimicrobial agents may be added to prevent bacteria from growing on and/or in the cast 10, and/or the like, and/or combinations thereof.

In an embodiment, in addition to heating the shape memory polymer 12 to switch it from its permanent shape 12' to its primary temporary shape 12", a force may also be applied inside the hollow interior portion 16' to allow such transformation. An example of a suitable force that may be applied inside the hollow interior portion 16' includes pressure. In some instances, the pressure inside the hollow interior portion 16' may be increased by introducing therein gas, water, or other material. Such a material may be constrained in an inflatable bladder that is inserted into the portion 16'. Such a bladder may be expanded when exposed to pressure, thereby forcing the permanent shape 12' to open up. Yet another example of a suitable force that may be applied to the shape memory polymer 12 includes a mechanical force. Such mechanical forces may be applied by, e.g., injecting a material inside the hollow interior portion 16', applying a tensile force to an outer surface of the shape memory polymer 12 (e.g., pulling the shape memory polymer 12 open using gripping features attached to the shape memory polymer 12), or the like. It is to be understood that when one or more forces are applied in addition to the heating of the shape memory polymer 12, the heat and the force may be applied sequentially or simultaneously.

It is to be understood that the deformation process (i.e., obtaining the primary temporary shape 12″) may be part of the manufacturing process of the cast 10 such that the end product is the shape memory cast 10 in its primary temporary shape 12″. When ready to be used, the cast 10 in its primary temporary shape 12″ is placed over the limb 14 and heated above its switching temperature to attempt recovery of the permanent shape 12′. During attempted recovery of the permanent shape 12′, the polymer 12 adopts the secondary temporary shape 12‴ when it conforms to the limb 14, which has a larger diameter than the permanent shape 12′.

If the deformation and setting process to achieve the primary temporary shape 12″ is not part of the manufacturing process, then deforming and heating the shape memory polymer 12 (such as described above for switching and setting the permanent shape 12′ of the shape memory polymer 12 to its primary temporary shape 12″) may be used post manufacturing. It is to be understood, however, that another means for deforming the shape memory polymer 12 in its permanent shape 12′ could also be used. In this example, deformation may be accomplished to directly achieve the secondary temporary shape 12‴ by sliding the shape memory polymer 12 in its permanent shape 12′ around the limb 14, similarly to a sleeve, while maintaining a temperature which enables substantially easy deformation of the polymer 12 (at or above its switching temperature). Once in place on the limb 14, the heat is maintained for some time to allow for the shape memory polymer 12 to apply optimal pressure to the limb 14 by continuing to attempt to revert to its permanent shape 12′ and achieving the secondary temporary shape 12‴.

In other instances, once the shape memory polymer 12 has been changed from its permanent shape 12′ into its primary temporary shape 12″, the primary temporary shape 12″ may be fixed or otherwise set by cooling the shape memory polymer 12 to a temperature below its switching temperature. It is to be understood that any temperature below the switching temperature of the shape memory polymer 12 will suffice. In a non-limiting example, the shape memory polymer 12 is cooled to a temperature ranging from about 10° to about 20° below its switching. It is to be understood that the temperature constraints depend, at least in part, on the underlying body temperature of the patient. At the body temperature, it is desirable that the cast 10 in the secondary permanent shape 12‴ maintain its shape fixity performance. As such, depending on the patient (e.g., human, other animal, etc.), it may be desirable that the switching temperature be about 45° C. to about 55° C. (wherein about indicates plus or minus 0.5 degrees). Furthermore, the temperature constraints also depend, at least in part, on the fact that if the cooling temperature is too close to the switching temperature of the shape memory polymer 12, reversion of the shape memory polymer 12 into, e.g., the secondary temporary shape 12‴ may undesirably occur too early. In a non-limiting example, the cooling temperature is at least about 10° C. lower than the switching temperature of the shape memory polymer 12.

Referring now to FIG. 1C, the example of the method further includes at least partially surrounding the limb 14 (e.g., when the cast is for a nose, when the cast includes an aperture for a thumb or tail, when the cast is an incomplete cylinder, etc.) with the shape memory polymer 12 in its primary temporary shape 12″. In an example, the limb 14 is positioned inside the hollow interior portion 16″ of the shape memory polymer 12 in its primary temporary shape 12″ so that the entire circumference of the limb 14 is surrounded by the shape memory polymer 12 (e.g., if the shape memory polymer 12 is completely cylindrically or substantially cylindrically-shaped). It is to be understood, however, that in instances where the primary temporary shape 12″ of the shape memory polymer 12 is an incomplete cylinder (as described hereinabove), the shape memory polymer 12 may surround part of the injured limb 14.

After the limb 14 is positioned inside the hollow interior portion 16″ of the shape memory polymer 12, the shape memory polymer 12 is deformed into the secondary temporary shape 12‴ (as shown in FIG. 1D). The deforming of the shape memory polymer from its primary temporary shape 12″ into its secondary temporary shape 12‴ occurs spontaneously in response to heating the shape memory polymer 12 to a temperature above its switching temperature. Heating may be accomplished using any of the heating techniques described above. As described hereinabove, when the shape memory polymer 12 in its primary temporary shape 12″ is heated at or above the switching temperature, the shape memory polymer 12 will automatically attempt to revert back into its permanent shape 12′. However, because the injured limb 14 is positioned inside the hollow interior portion 16″ of the shape memory polymer 12 during the attempted reversion back into the permanent shape 12′, the limb 14 acts as a reversion constraint and actually prevents the shape memory polymer 12 from reaching its permanent shape 12′. The shape memory polymer 12 is therefore reverted to a point at which it can no longer change (i.e., it contacts and conforms to the limb 14). As briefly mentioned hereinabove, this point is referred to as the secondary temporary shape 12‴, which conforms to the then-current shape of the injured limb 14. In other words, the secondary temporary shape 12‴ is a shape of the shape memory polymer 12 having a size that is between the sizes of the primary temporary shape 12″ and the permanent shape 12′. In one example, the shape memory polymer 12 in the secondary temporary shape 12‴ is also cylindrically or substantially cylindrically-shaped, and has a diameter $D_3$ that is smaller than the diameter $D_2$ of the primary temporary shape 12″ but is larger than the diameter $D_1$ of the permanent shape 12′.

Once the shape memory polymer has been partially reverted into the secondary temporary shape 12‴, the shape memory polymer 12 is cooled to a temperature below its switching temperature. At this temperature, the shape memory polymer 12 is set into its secondary temporary shape 12‴, thereby forming the medical cast 10 (as also shown in FIG. 1D).

FIGS. 2A through 2D together schematically depict a method of reusing the medical cast 10. Referring now to FIGS. 2A and 2B together, the shape memory polymer 12 in its secondary temporary shape 12‴ is removed from the limb 14 by heating the memory polymer 12 in its secondary temporary shape 12‴ until it is deformable enough to be removed from the limb 14. Once deformable, the cast 10 is soft enough (i.e., has a relatively low modulus) to be slid off of the limb 14. In some instances, it may be desirable to convert the shape memory polymer 12 back into, for example, the primary temporary shape 12″ or any other temporary shape that is larger than the secondary temporary shape 12‴. This may be accomplished, for example, by heating the shape memory polymer 12 to a temperature above its switching temperature and applying a force on the interior of the cast 10 (e.g., by inserted some object (e.g., a spatula) or pressure (e.g., pressurizable air balloons) between the cast 10 and the limb 14).

The limb 14 is then removed from the shape memory polymer 12 by sliding the limb 14 out from inside the hollow interior portion 16", or as mentioned above, by sliding the cast 10 off of the limb 14.

After the limb 14 has been removed from the shape memory polymer 12 in its primary temporary shape 12", the shape memory polymer 12 may i) be reused for another injured limb (identified as reference numeral 14' in FIG. 2D) having a different shape than the original injured limb 14 (e.g., if the polymer 12 is a thermoplastic resin), ii) reused for another injured limb 14 having the same shape or a similar shape (e.g., a forearm and a shin) as the original injured limb 14 (e.g., if the polymer 12 is a thermoset and/or thermoplastic resin), iii) sterilized and stored for subsequent reuse in one of the previously mentioned manners, or iv) discarded or used in some other desirable manner (e.g., kept as a souvenir).

If one decides to use reuse the shape memory polymer cast 10 for another injured limb 14, the method described hereinabove may be repeated to set the cast 10 on the other limb 14. However, if one is able to (i.e., the cast 10 is formed of a thermoplastic resin, as the permanent shape of thermoset materials cannot be reset) and decides to reuse the shape memory polymer cast for another injured limb, the method further includes readjusting the permanent shape 12' of the shape memory polymer 12 so that the permanent shape 12' (and thus the primary temporary 12" and secondary temporary 12''' shapes) conforms to the shape of the other limb 14'.

Referring now to FIG. 2C, the readjusting of the permanent shape 12' of the thermoplastic resin-based shape memory polymer 12 may be accomplished by positioning the shape memory polymer 12 in a molding tool 18 (also referred to herein as a "mold") having the general shape of the other limb 14'. As previously mentioned, the readjusting technique disclosed herein is not suitable for casts 10 formed of thermoset materials.

Readjusting is generally desirable when the shape of the two limbs 14, 14' are completely different. In some instances, even when the limbs 14, 14' are different, readjusting may not be necessary if the shapes of the limbs 14, 14' are similar enough that the cast 10 is suitable as it was used for one of the limbs 14. Once positioned in the molding tool 18, the shape memory polymer 12 is heated. It is to be understood that the temperature at which the shape memory polymer 12 is heated inside the mold 18 depends, at least in part, on the thermoplastic material used for the shape memory polymer 12. Generally, heating is accomplished at a temperature above the highest melting temperature of the thermoplastic polymer 12. In most instances, the highest melting temperature of the polymer 12 is significantly higher than the switching temperature of the polymer 12. The "highest melting temperature" refers to the greatest temperature at which the polymer 12 actually melts, thereby enabling it to be molded, or remolded.

During the heating step of the readjusting method, pressure is applied to the melting thermoplastic resin-based shape memory polymer 12 such that the shape memory polymer 12 conforms to the mold 18 shape. Pressure (e.g., directly pressurized air or an inflated/pressurized internal bladder) is introduced into the mold (e.g., inside the cavity 16', 16" of the melting shape memory polymer 12), and the polymer 12 flows within the mold such that it conforms to the shape of the mold. The shape memory polymer 12, now in the new permanent shape 12'$_A$, is cooled to a temperature below its highest melting temperature and below its switching temperature (e.g., its glass transition temperature or a lower melting temperature) to set the shape memory polymer 12 in its new permanent shape 12'$_A$.

The reset shape memory polymer 12 (i.e., having its new permanent shape 12'$_A$) may then be used to set the cast 10' on the other limb 14' (as shown in FIG. 2D). The cast 10' may be set on the limb 14' similarly to the method described above in connection with the FIG. 1 series. It is to be understood that in this example, however, the temporary shapes of the reset shape memory polymer 12 will resemble the new permanent shape 12'$_A$.

The methods for using described hereinabove effectively treat the injured limb 14, 14'. The treatment method includes disposing the shape memory polymer medical cast 10, 10', in its primary temporary shape 12", around the injured limb 14, 14' and reverting the shape memory polymer cast 10, 10' from the primary temporary shape 12", toward the permanent shape 12', into the secondary temporary shape 12''', such that the polymer 12 conforms to the injured limb 14, 14'.

It is to be understood that the shape memory polymer medical cast 10, 10' may be disposed on the inured limb 14, 14' once and then removed after the healing process is complete. The shape memory polymer cast 10, 10' may also advantageously be reheated, such that it is automatically readjusted one or more times during the healing process (after initially disposing the cast 10, 10' on the limb 14, 14'). At each re-heating stage, the polymer 12 attempts to revert to its smaller permanent shape 12', 12'$_A$, thereby creating yet another temporary shape (not shown in the Figures). As such, the cast 10, 10' may conform to the limb 14, 14' and may continuously apply a suitable amount of pressure to the limb 14, 14' throughout the healing process. For example, if swelling dissipates during the healing, the cast 10, 10' may be readjusted to yet another temporary shape so that the cast 10, 10' conforms to the limb 14, 14' having the reduced swelling. This may advantageously quicken the healing process and contribute to proper healing. Readjusting the cast 10, 10' further saves time and materials, as old casts do not have to be removed and discarded, nor do new casting materials have to be applied.

While several embodiments have been described in detail, it will be apparent to those skilled in the art that the disclosed embodiments may be modified. Therefore, the foregoing description is to be considered exemplary rather than limiting.

The invention claimed is:

1. A method of using a medical cast for a limb of a subject, the method comprising:
    providing a shape memory polymer in a permanent shape, the permanent shape corresponding to a general shape of the limb but having a diameter smaller than a diameter of the limb;
    converting the shape memory polymer from the permanent shape into a primary temporary shape, the primary temporary shape having a diameter that is larger than both a diameter of the permanent shape and a diameter of the limb;
    at least partially surrounding the limb with the shape memory polymer in the primary temporary shape;
    heating the shape memory polymer, thereby causing the primary temporary shape to i) attempt to revert to the permanent shape, and ii) conform to a secondary temporary shape having a diameter smaller than the diameter of the primary temporary shape and larger than that of the permanent shape, wherein the shape memory polymer in the secondary temporary shape conforms to the limb;

removing the shape memory polymer from the limb by converting the shape memory polymer from the second temporary shape to the primary temporary shape;

reusing the shape memory polymer for an other limb having a different shape than the limb; and readjusting the permanent shape of the shape memory polymer such that the adjusted permanent shape conforms to the shape of the other limb.

2. The method as defined in claim 1, further comprising cooling the shape memory polymer to a temperature below a switching temperature of the shape memory polymer to set the shape memory polymer in the secondary temporary shape.

3. The method as defined in claim 1 wherein the converting of the shape memory polymer from the permanent shape into the primary temporary shape is accomplished by:

heating the shape memory polymer to a temperature above its switching temperature; and deforming the shape memory polymer.

4. The method as defined in claim 3 wherein heating is accomplished by exposing the shape memory polymer to i) directly-applied heat from at least one of: a fluid heated to the temperature above the switching temperature of the shape memory polymer, or a heating device; ii) indirectly-applied heat emitted from active materials present in the shape memory polymer upon exposure to an external stimulus other than heat; iii) irradiation; or iv) combinations of i, ii, and iii.

5. The method as defined in claim 1 wherein the permanent shape, the primary temporary shape, and the secondary temporary shape are cylindrically-shaped, and wherein each of the cylindrically-shaped permanent shape, the cylindrically-shaped primary temporary shape, and the cylindrically-shaped secondary temporary shape includes a hollow interior portion defined by the shape memory polymer and having the respective diameter.

6. The method as defined in claim 5 wherein at least partially surrounding the limb with the shape memory polymer includes positioning the limb in the hollow interior portion of the shape memory polymer in the cylindrically-shaped primary temporary shape.

7. The method as defined in claim 1 wherein the heating of the shape memory polymer is accomplished at a temperature above a switching temperature of the shape memory polymer.

8. The method as defined in claim 1 wherein the shape memory polymer is formed from a thermoplastic material, and wherein the readjusting of the permanent shape of the shape memory polymer includes:

positioning the shape memory polymer in a mold having the general shape of the other limb;

heating the shape memory polymer to a temperature above its highest melting temperature, thereby rendering the shape memory polymer flowable;

applying pressure, thereby causing the flowable shape memory polymer to conform to the mold shape; and cooling the shape memory polymer to a temperature below its highest melting temperature, thereby setting the adjusted permanent shape.

9. The method as defined in claim 1 wherein the shape memory polymer is formed at least from a thermoset material.

10. The method as defined in claim 1 wherein the shape memory polymer is perforated, porous, made from a foam, or combinations thereof.

11. The method medical defined in claim 1 wherein the shape memory polymer is formed from an epoxy material, and wherein the shape memory polymer is transparent.

12. The method as defined in claim 1 wherein the shape memory polymer further includes inorganic fillers, fibers, or combinations thereof.

13. A method of treating an injured limb of a subject, the method comprising:

disposing a shape memory polymer medical cast, in its primary temporary shape, around the injured limb, the shape memory polymer medical cast having i) a permanent shape corresponding to a shape of the injured limb but having a diameter smaller than a diameter of the limb, and ii) the primary temporary shape that has a diameter that is larger than both a diameter of the permanent shape and a diameter of the injured limb;

attempting to revert the shape memory polymer medical cast from the primary temporary shape into the permanent shape, whereby while reverting, the shape memory polymer medical cast conforms to the injured limb and takes on a secondary temporary shape;

removing the shape memory polymer from the injured limb by converting the shape memory polymer from the secondary temporary shape to the primary temporary shape or an other shape of a larger size than the secondary temporary shape;

reusing the shape memory polymer for treating an other injured limb having a different shape than the limb; and readjusting the permanent shape of the shape memory polymer medical cast such that the adjusted permanent shape conforms to the shape of the other injured limb.

14. The method as defined in claim 13 wherein the shape memory polymer is formed of a thermoplastic material or a thermoset material, and further includes inorganic fibers, fillers, or combinations thereof.

15. The method as defined in claim 13 wherein the readjusting of the permanent shape of the shape memory polymer includes:

positioning the shape memory polymer medical cast in a mold having the general shape of the other injured limb;

heating the shape memory polymer medical cast to a temperature above its highest melting temperature, thereby rendering shape memory polymer medical cast flowable;

applying pressure, thereby forcing the flowable shape memory polymer medical cast to conform to the mold shape; and cooling the shape memory polymer medical cast to a temperature below its highest melting temperature, thereby setting the adjusted permanent shape.

16. The method as defined in claim 13 wherein the attempting to revert is accomplished via heating the shape memory polymer medical cast at a temperature above its switching temperature.

* * * * *